United States Patent
Beuthan et al.

(10) Patent No.: US 6,833,915 B2
(45) Date of Patent: Dec. 21, 2004

(54) OPTICAL DIAGNOSIS SYSTEM FOR SMALL ANIMAL IMAGING

(75) Inventors: Jürgen Beuthan, Berlin (DE); Arne Hengerer, Erlangen (DE); Tobias Jochum, Berlin (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 62 days.

(21) Appl. No.: 10/188,745

(22) Filed: Jul. 5, 2002

(65) Prior Publication Data

US 2003/0035104 A1 Feb. 20, 2003

(30) Foreign Application Priority Data

Jul. 6, 2001 (DE) .......................................... 101 32 808

(51) Int. Cl.⁷ .............................. G01N 21/64; G01J 3/30
(52) U.S. Cl. ....................... 356/318; 356/72; 250/458.1
(58) Field of Search ............................ 356/318, 72–73; 250/458.1–461.2; 600/407

(56) References Cited

U.S. PATENT DOCUMENTS

| | | | | |
|---|---|---|---|---|
| 3,313,290 A | * | 4/1967 | Chance et al. | 356/317 |
| 5,955,736 A | * | 9/1999 | Robinson et al. | 250/458.1 |
| 6,126,901 A | * | 10/2000 | Patch et al. | 422/64 |
| 6,272,440 B1 | * | 8/2001 | Shakespeare et al. | 356/73 |
| 2001/0021063 A1 | * | 9/2001 | Knebel | 250/459.1 |

* cited by examiner

Primary Examiner—F. L. Evans
Assistant Examiner—Kara Geisel
(74) Attorney, Agent, or Firm—Young & Thompson

(57) ABSTRACT

Optical diagnosis system for small animal imaging, in which the animal which has been arranged on a bearing plate and treated with an activatable optical contrast medium is irradiated by an excitation source and the resulting fluorescent radiation that is radiated back is detected by a detector system, in which case the bearing plate is designed as a radiation-transparent window (13) for a reference radiation—generated by a second marker of the contrast medium—for the detection of the initial concentration of the inert contrast medium.

18 Claims, 1 Drawing Sheet

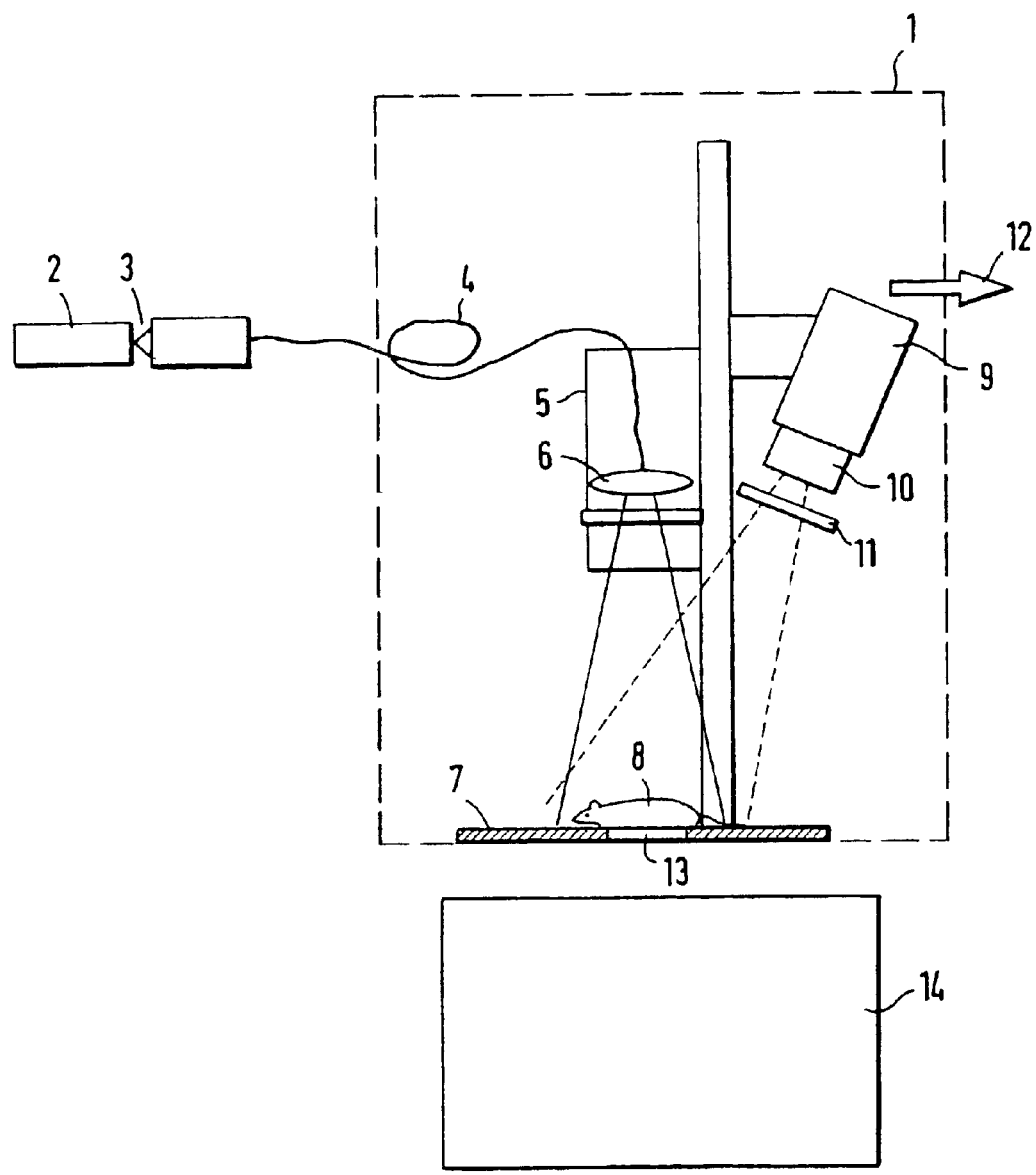

OPTICAL DIAGNOSIS SYSTEM FOR SMALL ANIMAL IMAGING

FIELD OF THE INVENTION

The invention relates to an optical diagnosis system for small animal imaging, in which the animal which has been arranged on a bearing plate and treated with an activatable optical contrast medium is irradiated by an excitation source and the resulting fluorescent radiation that is radiated back is detected by means of a detector system.

BACKGROUND OF THE INVENTION

In examinations of metabolic functions on a living small animal, use is made of activatable optical contrast media which fluoresce in the near infrared. The contrast medium is inert in healthy tissue and is activated, that is to say transferred into a fluorescent state, only in the target tissue, for example a tumor, by illness-correlated metabolic activities (enzymatic processes). Through a highly selective activation mechanism, a very high signal-to-noise ratio is achieved with this contrast medium. The metabolic activity can be quantified by measurement after determination of the activation rate. However, this requires knowledge not only of the concentration of the activated contrast medium that is to be determined by the fluorescent signal but also of the initial concentration of the inert contrast medium in the target tissue. This value cannot be calculated from the injected dose, but rather has to be determined experimentally, which can preferably be effected by a second continuously signaling marker which does not interfere with the activation signal, such as a radioisotope marker, for example. Such a method presupposes a dual imaging, in which case, hitherto, after the determination of the activated contrast medium by measurement of the fluorescent radiation, the animal has first had to be transferred into a second imaging system, in order to detect the second continuously signaling marker of the contrast medium. In addition to the additional burden imposed by this repositioning of the animal, which can lead to considerable health problems, these measurements in two different imaging systems make the superposition of the two images more difficult, since artificial or anatomic markers have to be used for the registration. Furthermore, the measurement accuracy is impaired, particularly in the case of parameters that fluctuate greatly with respect to time in the target tissue (high enzymatic conversion and fast pharmacodynamics).

SUMMARY OF THE INVENTION

The invention is therefore based on the object of configuring an optical diagnosis system of the type mentioned in the introduction in such a way that working with two imaging systems between which the animal has to be transferred is obviated.

In order to achieve this object, the invention provides for the bearing plate to be designed as a radiation-transparent window for a reference radiation—generated by a second marker of the contrast medium—for the detection of the initial concentration of the inert contrast medium.

According to the invention, then, the optical diagnosis system is designed in such a way that—through a coupling by means of the bearing plate designed as a radiation-transparent window—the imaging system for the second continuously signaling marker is integrated into the imaging system for the fluorescent radiation. This enables simultaneous measurement both of the fluorescent radiation and of the reference radiation, thereby producing a very high measurement accuracy, in conjunction with the simple registration of the two images, since, after all, they are in each case recorded with the same positioning of the animal.

The second marker could also be formed, in principle, by a second fluorescent marker for the inert contrast medium with an altered frequency. Preferably, however, the second marker is intended to be a radioisotope marker, the window, below which a gamma ray receiver is arranged, being gamma-ray-transmissive, but preferably NIR-opaque.

Such a window may comprise, for example, thin aluminum sheet or, alternatively, carbon fiber reinforced plastic.

The fluorescent radiation of the excitation source, which may be an infrared laser diode, for example, may be excitable and measurable in different directions in order to obtain 3D information, in which case depth information can be calculated from the measured values of at least two different reception angles. This can be effected automatically in the device by means of a corresponding algorithm and a corresponding design of the evaluation electronics.

BRIEF DESCRIPTION OF THE DRAWINGS

Further advantages, features and details of the invention emerge from the following description of an exemplary embodiment and with reference to the drawing, which diagrammatically shows the invention's optical diagnosis system for small animal imaging in combination with nuclear medicine imaging.

DETAILED DESCRIPTION OF THE INVENTION

The optical diagnosis system 1 with an infrared laser diode 2, which is connected via an optical coupling 3 and a fiber-optic cable 4 to the actual excitation system 5 with a lens 6, enables the small animal 8, arranged on a bearing plate 7, to be irradiated with an infrared radiation which initiates a fluorescent radiation in the target tissue, for example a tumor in the animal, which fluorescent radiation can be detected by means of a CCD camera 9 with lenses 10 and filters 11 placed in front of it. In this case, the detectable fluorescent radiation is based on the fact that a special optical contrast medium administered to the small animal is activated, that is to say transferred into a fluorescent state, in the target tissue by illness-correlated metabolic activities. The fluorescent radiation is then initiated in the diseased region by the excitation infrared radiation from the laser diode 2 and measured by means of the CCD camera, whereupon it is forwarded—indicated by the arrow 12—to an image processing stage.

According to the invention, the bearing plate 7 is provided with a radiation-transparent window 13, preferably a gamma-ray-transmissive radiation window, for example made of aluminum or glass fiber reinforced plastic, so that, at the same time as the optical imaging using the fluorescent radiation of the activatable optical contrast medium inside the small animal 8 to be examined, a second examination can be effected using a second marker of the contrast medium. This preferably involves a radioisotope marker, that is to say a continuously signal-generating marker of the contrast medium, which, irrespective of whether or not an illness-correlated metabolic activity has activated the first fluorescent marker in the target region, allows measurement of the total content of contrast media in the respectively detected region of the small animal. The measurement result via this gamma radiation camera 14 below the window 13 enables the activation rate to be determined and thus the metabolic activity to be quantified. The dimensioning of the window 13 is preferably such that the entire object can be detected by the measurement.

What is claimed is:

1. An optical diagnosis system for an animal imaging, comprising:

a bearing plate on which the animal may be arranged for treatment by an inert optical contrast medium having an activatable first marker and a non-activatable second marker;

an excitation source for irradiating the animal and the inert optical contrast medium to initiate a fluorescent radiation in tissue of the animal;

a detector system for detecting the resulting fluorescent radiation as radiated back from the tissue of the animal, wherein, the detector system is positioned above the bearing plate, the bearing plate is a radiation transparent window for a reference radiation, generated by a non-activatable second marker, for the detection of an initial concentration of the inert contrast medium in the tissue of the animal, and the second marker is one of a radioisotope marker and a fluorescent marker with an altered frequency related to the activatable first marker.

2. The optical diagnosis system as claimed in claim 1, further comprising the inert optical contrast medium.

3. The optical diagnosis system as claimed in claim 2, wherein the window (13) is NIR-opaque.

4. The optical diagnosis system as claimed in claim 3, wherein the window (13) comprises thin aluminum sheet.

5. The optical diagnosis system as claimed in claim 3, wherein the window (13) comprises carbon fiber reinforced plastic.

6. The optical diagnosis system as claimed in claim 1, wherein the excitation source comprises an infrared laser diode connected via an optical coupling and a fiber-optic cable to an excitation system with a lens.

7. The optical diagnosis system as claimed in claim 1, wherein the fluorescent radiation is excitable and measurable in different directions in order to obtain 3D information.

8. The optical diagnosis system as claimed in claim 1, characterized in that the excitation source is an infrared laser diode (2).

9. An optical diagnosis system for an animal imaging, comprising:

a bearing plate on which the living animal may be arranged for treatment by an inert optical contrast medium having an activatable first marker and a non-activatable second marker;

an excitation source for irradiating the animal and the inert optical contrast medium to initiate a fluorescent radiation in tissue of the animal;

a first detector system for detecting the resulting fluorescent radiation as radiated back from the tissue of the animal, wherein, the first detector system is positioned above the bearing plate, and a second detector system, positioned underneath the bearing table, for detecting a reference radiation by the non-activatable second marker, for detection of an initial concentration of the inert contrast medium in the tissue of the animal, the bearing plate being a radiation transparent window (13) for the reference radiation, and the second marker is one of a radioisotope marker and a fluorescent marker with an altered frequency related to the activatable first marker.

10. The optical diagnosis system as claimed in claim 9, wherein, the excitation source is an infrared laser diode.

11. The optical diagnosis system as claimed in claim 9, characterized in that the window (13) is NIR-opaque.

12. The optical diagnosis system as claimed in claim 11, characterized in that the window (13) comprises thin aluminum sheet.

13. The optical diagnosis system as claimed in claim 11, characterized in that the window (13) comprises carbon fiber reinforced plastic.

14. The optical diagnosis system as claimed in claim 9, characterized in that the fluorescent radiation is excitable and measurable in different directions in order to obtain 3D information.

15. The optical diagnosis system as claimed in claim 14, characterized in that the excitation source is an infrared laser diode (2).

16. The optical diagnosis system as claimed in claim 11, characterized in that the excitation source is an infrared laser diode (2).

17. The optical diagnosis system as claimed in claim 12, characterized in that the excitation source is an infrared laser diode (2).

18. The optical diagnosis system as claimed in claim 13, characterized in that the excitation source is an infrared laser diode (2).

* * * * *